(12) United States Patent
Schwarz

(10) Patent No.: US 9,259,141 B2
(45) Date of Patent: Feb. 16, 2016

(54) ENDOSCOPE

(71) Applicant: Karl Storz GmbH & Co. KG, Tuttlingen (DE)

(72) Inventor: Peter Schwarz, Tuttlingen-Nendingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 0 days.

(21) Appl. No.: 13/951,289

(22) Filed: Jul. 25, 2013

(65) Prior Publication Data

US 2014/0031626 A1  Jan. 30, 2014

(30) Foreign Application Priority Data

Jul. 25, 2012 (DE) .......................... 10 2012 106 755

(51) Int. Cl.
*A61B 1/00* (2006.01)
*A61B 1/005* (2006.01)
*A61B 1/018* (2006.01)
*A61B 1/045* (2006.01)
*A61B 1/12* (2006.01)
*A61B 1/04* (2006.01)

(52) U.S. Cl.
CPC .............. *A61B 1/0052* (2013.01); *A61B 1/0016* (2013.01); *A61B 1/0057* (2013.01); *A61B 1/00114* (2013.01); *A61B 1/00117* (2013.01); *A61B 1/00119* (2013.01); *A61B 1/00165* (2013.01); *A61B 1/018* (2013.01); *A61B 1/045* (2013.01); *A61B 1/12* (2013.01)

(58) Field of Classification Search
CPC ...... A61B 1/0066; A61B 1/133; A61B 1/147; A61B 1/16; A61B 1/51; A61B 1/52; A61B 1/57

USPC ......... 600/149, 145, 146, 139, 131, 114, 117, 600/147, 148; 604/95.01
See application file for complete search history.

(56) References Cited

U.S. PATENT DOCUMENTS

| 4,499,895 A | 2/1985 | Takayama |
|---|---|---|
| 4,503,842 A | 3/1985 | Takayama |
| 4,721,099 A | 1/1988 | Chikama |

(Continued)

FOREIGN PATENT DOCUMENTS

| EP | 1825801 A1 | 8/2007 |
|---|---|---|
| EP | 2324755 A1 | 5/2011 |
| WO | 2012063880 A1 | 5/2012 |

*Primary Examiner* — Anhtuan T Nguyen
*Assistant Examiner* — Timothy J Neal
(74) *Attorney, Agent, or Firm* — Whitmyer IP Group LLC

(57) ABSTRACT

An endoscopic instrument includes a manipulating piece having a manipulating element, an instrument shaft having a section that is manipulable, wherein the shaft is coupled to the manipulating piece, a positioning element having a first rotational axis, a pulling element coupled to the positioning element and the section of the shaft, such that displacement of the positioning element actuates the section by transmitting a force via the pulling element, and an actuator coupled to the positioning element, such that actuation of the actuator displaces the positioning element by transmitting a force from the actuator to the positioning element. The manipulating element is coupled to the positioning element such that a force exerted onto the manipulating element transfers onto the positioning element and displaces the positioning element. The first rotational axis and a second rotational axis of the actuator are arranged at an angle less than 90° relative to one another.

18 Claims, 5 Drawing Sheets

(56) References Cited

U.S. PATENT DOCUMENTS

| | | |
|---|---|---|
| 5,060,632 A | 10/1991 | Hibino et al. |
| 6,932,761 B2 | 8/2005 | Maeda et al. |
| 7,331,924 B2 | 2/2008 | Arai et al. |
| 2007/0255102 A1* | 11/2007 | Maruyama .................. 600/146 |
| 2009/0227841 A1* | 9/2009 | Miyako et al. ............... 600/139 |
| 2010/0125166 A1* | 5/2010 | Henzler ....................... 600/109 |
| 2010/0210908 A1 | 8/2010 | Ashida et al. |
| 2011/0009698 A1* | 1/2011 | Ashida et al. ................ 600/118 |
| 2011/0088498 A1* | 4/2011 | Ettwein et al. ............. 74/479.01 |

* cited by examiner

ENDOSCOPE

BACKGROUND OF THE INVENTION

The present invention relates to an endoscopic instrument comprising a manipulating piece having a manipulating element, an instrument shaft having a section to be manipulated by a user, wherein the instrument shaft is coupled to the manipulating piece, further comprising a positioning element having a first rotational axis, a pulling element which is mechanically coupled to the positioning element and the section of the instrument shaft, such that a displacement of the positioning element may achieve an actuation of the section by transmitting a force via the pulling element, and further comprising an actuator coupled to the positioning element, such that an actuation of the actuator may provide for a displacement of the positioning element by transmitting a force from the actuator to the positioning element, wherein the actuator comprises a second rotational axis, and wherein the manipulating element is configured such that a user may displace the positioning element by actuating the manipulating element and wherein the manipulating element is mechanically coupled to the positioning element such that a force exerted by the user onto the manipulating element may at least be partially transferred onto the positioning element and may provide for a displacement of the positioning element.

Endoscopic instruments having a flexible or rigid endoscope shaft are used in the industry as well as in the medical field. For example, flexible endoscopes are used in veterinary medicine when performing a gastro-endoscopic examination on larger animals. These endoscopes typically have at their distal end of the endoscope shaft a distal end section which ends in an end piece. The end piece is a distal part of the endoscope which is inserted into the body under examination. Typically it comprises the distal end of endoscope optics and sometimes channels for suction, cleaning and tooling as well.

In order to obtain the largest possible flexibility regarding the spatial positioning of the end piece during examination, the end section of the endoscope shaft is typically configured to be deflectable. By deflecting or, more general, by actuating the section relative to the remaining instrument shaft, in particular by bending or curving, a piece of the instrument shaft, in particular the end piece, can be aligned as necessary. When applying deflection the user has to apply caution to ensure that no tissue surrounding the end section is damaged. It is therefore crucial that actuating the section can be controlled very precisely.

The deflection of the section is achieved for flexible and rigid endoscopes according to the prior art via a pulling element, in particular via Bowden cables. The pulling element is coupled to a positioning element, in particular a steering gear. The pulling element is typically attached to a string wheel, which is configured to hold and guide a string looped around the wheel. By actuating the manipulating element at the manipulating piece of the endoscope the positioning element is displaced. A translatory displacement of the pulling element is achieved by a rotational displacement of the positioning element. The displacement of the pulling element in turn provides for a deflection of the section.

U.S. Pat. No. 4,499,895 shows an electric endoscope which is manipulated via a lever which is coupled to the positioning element. When the lever is displaced relative to the positioning element, a bending of the lever or a change in a resistance of a potentiometer is detected and thereby a support of the positioning element via an actuator is activated. The shown arrangement, however, cannot be handled well and requires a specific releasing mechanism in order to be able to manipulate the endoscope in case of a fault.

U.S. Pat. No. 7,331,924 is directed at an electric endoscope having a deflectable distal section. The manipulation of the endoscope is achieved via a track ball which is displaced via the thumb or the finger of a user and which displacement is detected via an electric circuit. Depending on the rotational displacement of the track ball, as chosen by the user, the control of a motor is determined in a deflection control, the motor providing for a displacement of the pulling element and thus a deflection of the distal section.

The disadvantage of such an electric endoscope is, however, that its manipulation is found to be less intuitive since the manipulation of an electric endoscope, for example when coming into contact with tissue, does not provide the same feedback as the user is used to from mechanical endoscopes. The same problem is present with electric endoscopes which are controlled via a joystick. As an example, reference is made to document U.S. Pat. No. 6,932,761. Electric endoscopes further have the disadvantage that they may be hard to retract from a cavity in case of a fault when the distal section is deflected.

For mechanical endoscopes the deflection of the section is achieved only via a mechanical force exerted by the user onto a handle provided at the outside of the manipulating piece of the endoscope. To achieve this, the positioning element is typically arranged in a fixed manner on a drive shaft of the handle. When the user actuates the handle, a rotational displacement of the positioning element results and in turn a translatory displacement of the pulling element.

Purely mechanical endoscopes may require significant forces for an actuation depending on the length of the endoscope and the spatial position of the endoscope shaft. In addition, the mechanical actuation of the section automatically provides a certain resetting force in the direction of the non-deflected position (null position) of the endoscope. Further, the section provides during deflection a spring-damper-system in connection with the pulling element which stores energy during tensioning and releases energy when relaxing. This may result in a lag in the displacement when starting or an additional displacement when ending the deflection of the end section. This results in the user setting the deflection of the section in order to view a certain location may only approximately or iteratively set the deflection.

It is therefore an object of the present invention to improve an endoscopic instrument as mentioned before such that the user obtains support during manipulation as is the case for an electric actuation, without the user losing the mechanical feedback of the endoscope. It is a further object that the endoscope can be continuously manipulated even when a fault of the electronic control occurs.

SUMMARY OF THE INVENTION

According to one aspect of the invention an endoscopic instrument is provided, the instrument comprising a manipulating piece having a manipulating element, an instrument shaft having a section to be manipulated by a user, wherein the instrument shaft is coupled to the manipulating piece, further comprising a positioning element having a first rotational axis, a pulling element which is mechanically coupled to the positioning element and the section of the instrument shaft, such that a displacement of the positioning element may achieve an actuation of the section by transmitting a force via the pulling element, and further comprising an actuator coupled to the positioning element, such that an actuation of the actuator may provide for a displacement of the positioning element by transmitting a force from the actuator to the positioning element, wherein the actuator comprises a second rotational axis, and wherein the manipulating element is configured such that a user may displace the positioning element by actuating the manipulating element and wherein the manipulating element is mechanically coupled to the positioning element such that a force exerted by the user onto the manipulating element may at least be partially transferred onto the positioning element and may provide for a displacement of the positioning element, and wherein the first rotational axis and the second rotational axis are arranged at an angle of less than 90°.

According to a further aspect of the invention, due to the arrangement of the first and second rotational axes a motor-supported manipulation of the endoscope is possible, but in case of a fault a purely manual manipulation is possible as well without an additional releasing mechanism.

It may be advantageous if the angle between the first and second rotational axes is less than 85°, preferably less than 75°, more preferably less than 60° and in particular less than 45°. If gear rings are used for providing the operational engagement between the actuator and the positioning element, the angle may be provided in particular by helical gear ring. For some embodiments it is specifically advantageous if the angle between the first and second rotational axes is at least approximately 0°, so that the axes are at least approximately parallel to one another or that the axes coincide with one another or are co-extensive with one another.

According to a further aspect, due to the positioning element being coupled with the actuator, in particular an electric motor, and the manipulating element, a force provided by the actuator as well as by the manipulating element can be transmitted onto the positioning element and the displacement of the positioning element may be obtained.

During normal operation the user actuates the manipulating element in order to achieve an actuation of the section. The displacement of the manipulating element is detected, and the actuator is controlled such that the displacement of the positioning element caused by the manipulating element is supported. If no further displacement of the manipulating element takes place, no further displacement of the positioning element via the actuator takes place.

If the actuator fails due to a fault, the endoscope can still be manipulated, since a force can be exerted onto the positioning element via the manipulating element. The possibility of actuating the section is maintained even in case of a fault. Then, only the support via the actuator will be missing.

The actuator is preferably arranged in the manipulating piece of the endoscope. The positioning element is preferably arranged in the manipulating piece of the endoscope. The pulling element is preferably embodied as a Bowden cable, which is preferably looped around the positioning element. The positioning element is preferably embodied as a string wheel. The actuator is preferably provided as an electric motor, which may comprise, in particular, a gear or a transmission.

When explaining the various aspect and reference is made to an actuation or a displacement, such expressions are understood to comprise a twisting actuation and/or a rotational displacement. However, when using appropriate sliders or pushers, embodiments may be achieved where a translatory or linear actuation or displacement takes place. The corresponding transmission of force between the manipulating element and the positioning element or the actuator and the positioning element can be achieved via one or more points where at each of them a force or a resulting torque is transmitted.

The endoscopic instrument may preferably be embodied as an endoscope wherein the instrument shaft is embodied as an endoscope shaft. It may further be preferred if the section that can be actuated is a deflectable distal section. The wording of actuation or actuating comprises in particular cutting, clamping and turning, and more preferably deflecting. It may further be preferred to embody the positioning element and the pulling element as one integral piece in particular when using claws or such where positioning element and pulling element are embodied as push-pull-rod.

In a preferred embodiment the endoscopic instrument comprises a second positioning element, a second pulling element mechanically coupled to the second positioning element and the section of the instrument shaft such that a displacement of the second positioning element may provide for an actuation of the section by transmitting a force via the second pulling element, and further comprising a second actuator coupled to the second positioning element such that an actuation of the second actuator may provide for a displacement of the second positioning element by transmitting the force from the second actuator onto the second positioning element, wherein the manipulating element is embodied such that a user may obtain a displacement of the second positioning element by actuating the manipulating element, and wherein the manipulating element is mechanically coupled to the second positioning element such that a force exerted by the user onto the manipulating element is at least partially transmitted onto the second positioning element and may provide for the displacement of the second positioning element.

For this embodiment the manipulating element preferably comprises a first handle configured to displace the previously mentioned positioning element, also referred to as first positioning element, and a second handle configured to displace the second positioning element. Preferably, the actuation of the first handle results in a first movement of the section, in particular to a movement left/right, and the actuation of the second handle results in a second movement of the section, preferably in a movement up/down. Preferably, one of the handles is arranged on a hollow drive shaft in which a drive shaft of the other handle is arranged.

Therefore, the objects are achieved.

In a preferred refinement the positioning element comprises a first gear ring, the actuator comprises a second gear ring, and the first and second gear rings are coupled by force-fit, in particular they are arranged such that their teeth are meshing.

This refinement may provide for a good coupling between the positioning element and the actuator in particular in view of a rotational displacement of the positioning element. Further, such coupling is mechanically reliable and long-term robust.

In a further preferred refinement the positioning element and the actuator are coupled by a belt, a gear belt, a chain or by friction wheels.

According to a further preferred refinement the positioning element comprises a first gear ring, the manipulating element comprises a third gear ring, and first and third gear rings are coupled by force-fit, in particular they are arranged such that their teeth are meshing.

This refinement may provide for a good coupling between positioning element and the manipulating element in particular in view of a rotational displacement of the positioning element. Further, such coupling is mechanically reliable and long-term robust.

According to a further preferred refinement the manipulating element and the actuator are mechanically operationally coupled to one another such the force exerted by the user onto the actuating element may at least be partially transmitted onto the actuator.

In this refinement, there is a mechanical coupling among the manipulating element, the positioning element and the actuator. This ensures that the actuator and the manipulating element may transmit a force at the same time onto the positioning element. In case of a fault of the actuator an actuation of the manipulating element—without further design features—also results in a displacement of the actuator which may result in a certain resistance related to the displacement of the positioning element. However, when using an appropriate actuator and/or when applying additional design features, in particular a releasable coupling between the actuator and the positioning element, this influence may be kept small or negligible.

According to a further preferred refinement a control is provided to drive the actuator such that it can generate a force feedback for the user, in particular against the handle. This allows for a communication with the user. For example, certain positions or conditions may be indicated to the user with different vibrations of the actuator. Preferably, the actuator indicates the neutral position of the manipulating element to the user via a short braking impulse. In this context it is preferred that an angle measuring device is associated with the positioning element in order to detect the neutral position. It is further preferred that the actuator is controlled such that exceeding a threshold of the deflection force is indicated by vibrating. It is further preferred that external systems may transmit information regarding a safety-relevant condition (for example, an insufflation pressure being too high or exceeding a temperature) and to indicate this to the user via different frequencies of vibration by a corresponding control.

According to a further refinement the manipulating element comprises a handle and an engaging element, the handle and the engaging element being arranged such that they can be displaced relative to one another, and the handle and the engaging element are coupled with one another such that a displacement of the handle may result in a displacement of the engaging element.

For this refinement the engaging element is preferably operationally coupled to the positioning element. Since the handle and the engaging element may be displaced relatively to one another it can be easily determined whether the user is exerting a force onto the handle in order to control the actuation of the section. If such relative displacement is detected the corresponding driving of the actuator is preferably triggered.

The wording "corresponding driving" is to be understood such that the actuator supports the actuation desired by the user. If the user intends to displace the positioning element into a certain direction, for example clockwise, the actuator supports this displacement into the same direction. If the user intends to displace the positioning element into another direction, for example counterclockwise, the actuator supports the displacement in that same direction.

The relative displacement of handle and the engaging element relative to one another involves in particular that the handle may be subjected to a small rotational displacement to which the engaging element is not subjected at the same time and/or not in the same manner. It is preferred that the handle and the engaging element are arranged along the same axis and/or driving shaft. It is further preferred that the handle and the engaging element are fixed to the same driving shaft and that the possibility of a relative displacement may be obtained by an at least small twisting of the driving shaft in a portion between the position of the handle and the position of the engaging element.

In particular it is preferred that the handle and the engaging element are not fixedly connected via a drive shaft with one another, but that the handle is merely arranged concentrically without a fixed connection to the driving shaft of the engaging element or that it is concentrically arranged along a hypothetical extension of this drive shaft. In this case it is in particular ensured by a lose mechanical coupling of the handle and the engaging element that, at least after a certain relative displacement of the handle and the engaging element relative to one another, the displacement of the handle results in a displacement of the engaging element.

The relative displacement is preferably limited to a maximum of 10°, more preferred to a maximum of 3°, even more preferred to a maximum of 1° and in particular to a maximum of 0.3°. This is preferably achieved by the coupling arrangement described further down.

The handle is preferably embodied as a wheel, a lever or as a crank. Preferably, the handle and the engagement element are embodied as distinct parts, not as one piece. Preferably the relative displacement is performed by rotatorily displacing the handle and the engaging element, in particular without bending, skewing or twisting either the handle or the engaging element.

According to a further preferred refinement the manipulating element comprises a coupling arrangement having a first part and a second part, wherein one of the parts is connected to the handle and the other part is connected to the positioning element or the engaging element, wherein the parts are configured and arranged such that a transmission of a force between the handle and the positioning element or the handle and the engaging element may be obtained due to a transmission of a force between the first and the second parts.

This refinement allows for the handle to be twisted at least to a small degree relative to the positioning element or the engaging element and that a force may be transmitted from the handle onto the positioning element or the engaging element. In particular, force resulting in a rotational displacement of the handle may be at least partially transmitted onto the positioning element or the engaging element so that a rotational displacement of the positioning element or of the engaging element is obtained.

In a preferred refinement the coupling is provided via a combination of a groove and a projection which runs within the groove wherein the groove is arranged either at the handle or at the positioning element or the engaging element and wherein the projection is arranged at the corresponding other element. As long as the projection moves between the two ends of the groove, the handle and the positioning element or the engaging element may be displaced relative to one another. If the projection pushes against one of the ends of the groove, the displacement of the handle results in a displacement of the positioning element or the engaging element. It is preferred that the handle and the positioning element or the engaging element each perform a rotational displacement wherein the groove has the shape of a circular arc.

According to a further preferred refinement the coupling arrangement comprises a force measuring device configured to indicate whether a force is being exerted between the first part and the second part or to provide an indication related to the magnitude of a force exerted between the first part and the second part, in particular including an indication regarding the direction of the force being exerted.

This refinement allows to easily determine whether the user is displacing the handle in order to transmit a force the engaging element onto the positioning element. If such force is detected, the actuator is preferably actuated in order to support the desired displacement of the positioning element. It is preferred that the force is detected with its sign, for example forward/backward or clockwise/counterclockwise, so that the actuator my support a displacement of the positioning element in two directions.

In this context it is preferred that the force measuring device provides an indication of the magnitude of the force that is being exerted between the first part and the second part. If the indication shows that the force is small, the actuator will also provide a small support only. If the indication shows that the force is large, the actuator will provide a large supporting force as well.

The expressions "large support" and "small support" are to be understood in view of the force which the actuator exerts onto the positioning element. If the actuator is provided, preferably, as an electric motor, the electric motor will be driven with a larger current for a large support in comparison to when a small support is desired.

The indication may be provided in a simple way, preferably making a distinction between "no force", "small force" and "large force", as this may allow for a cost-sensitive and robust manufacturing of the force measuring device. For other refinements it may be preferred that the indication is provided in more than three, preferably more than five, more preferably more than ten steps and in particular continuously. Depending on the magnitude of the force a corresponding support is provided by the actuator.

Preferably, the measuring of the force is achieved by providing a pressure sensor.

According to a further preferred refinement a spring device is arranged at the first and/or the second part such that a force between the first part and the second part is transmitted via the spring device.

This refinement allows for a very intuitive manipulation since the user displaces the handle against a resistance of the spring device and thus receives a haptic feedback during the actuation of the handle. In particular, the user may feel how much the actuator will be actuated due to the displacement of the handle. The user may therefore precisely control the actuation of the section.

According to a further preferred refinement the first part comprises two elements and the second part is embodied as a projection being arranged between the two elements, and the first and the second parts are arranged relative to one another such that a displacement of the first part may result in a displacement of the second part.

This refinement has a certain free distance in which the projection may move between the two elements which are preferably provided as protruding elements. When the second part comes into contact with an element of the first part during its displacement, the first and second parts are moving together. This allows for a relative displacement of the handle and the engaging element. The displacement may be easily detected and the actuator may be driven correspondingly.

In a further preferred refinement the endoscope comprises a first angle measuring device embodied to provide an indication of a first angle position of a handle of the manipulating element.

This refinement allows for an advantageous driving of the actuator. For example, a table may be provided showing which actuation the actuator must receive, in particular which angle of rotation the actuator has to perform, in order to bring the positioning element into a position which the user intends to achieve based on the first angle position set at the handle. It is not mandatory to detect the first angle position directly at the handle. It is sufficient to measure the angle position of an element which follows the rotation of the handle, in particular due to a mechanical connection via axes or gear rings, so that the angle position of this element provides for an indication of the first angle position.

In addition, by measuring the first angle position at least twice at different times, a change of the first angle position can be calculated and the change of the first angle position may be used for driving the actuator. It is further preferred to measure the time interval between the measurements in order to obtain, by dividing the change in the first angle position by the time interval between the two measurements, the angular speed. It is preferred to have the actuator provide a large support if the angular speed is large and to have the actuator provide a small support if the angular speed is small.

According to a further preferred refinement the endoscope comprises a second angle measuring device configured to give an indication of a second angle position of the positioning element.

This refinement, too, allows for an advantageous driving of the actuator. If the second angle position of the positioning element is known, a difference between the second angle position and the first angle position can be determined and thus the required actuation of the actuator. For this refinement as well, the change in angle and/or the angular speed are considered when driving the actuator. It is not mandatory to detect the second angle position directly at the positioning element. Rather, it may be sufficient to measure the angle position of an element which follows the rotation of the positioning element, in particular due to a mechanical connection via axes or gear rings such that the angle position of this element provides for an indication regarding the second angle position.

According to a further preferred refinement the endoscope comprises a third angle measuring device configured to provide for an indication of a third angle position of the actuator.

According to a further preferred refinement the endoscope further comprises a fourth angle measuring device configured to provide for an indication of a fourth angle position of the engaging element.

For the last two refinements as well, see above, it is not mandatory to measure the third angle position directly at the actuator and/or to measure the fourth angle position directly at the engaging element. Further, it is to be appreciated that two or more of the angle measuring devices may be combined. The explanations made in the context of the first and second angle positions are applicable correspondingly to the third and fourth angle positions.

According to a further preferred refinement the endoscope comprises a control device configured to drive the actuator taking into account a first angle position of a handle of the manipulating element and a second angle position of a positioning element.

In this embodiment a difference between a first angle position of the handle and the second angle position of the positioning element is determined. If a difference is detected this is an indication that the user has to displace the handle relative to the positioning element and that the user wants to achieve a displacement of the positioning element. In this case the actuator is actuated in order to support the displacement of the positioning element. Preferably, the magnitude of the difference between the first angle position and the second angle position is taken into account when driving the actuator.

If the difference is large the actuator will provide a large support. If the difference is small the actuator will provide a small support. If the angular speed is taken into account as previously explained, it is preferred to have the actuator provide a large support if the angular speed is large and to have the actuator provide a small support if the angular speed is small.

According to a further preferred refinement the endoscope comprises a control device configured to drive the actuator such that the positioning element is maintained at a given position if the user does not exert a force on the manipulating element.

As has been explained before, the distal section in combination with the pulling element acts as a spring-damper-system. When a user stops actuating the handle, there is a tendency that the system slightly relaxes and the actuation of the section changes. According to the proposed refinement the actuator acts towards compensating this tendency. If no force is exerted onto the manipulating element by the user the actuator provides a force which maintains the positioning element in the position set by the user. The determination that the user is not exerting a force on the manipulating element is preferably made by using a force measuring device. Preferably, the first angle position and the second angle position being the same within a certain tolerance range is interpreted as an indication that the user is not exerting a force onto the manipulating element.

According to a further preferred refinement the endoscope comprises a control device configured to drive the actuator such that it exerts a force onto the positioning element which is at least in certain ranges at least approximately proportional to the force which the user exerts onto the manipulating element.

This refinement allows in a simple manner to achieve that the force exerted by the user onto the manipulating element results in a corresponding support by the actuator. Measuring the force is preferably performed by using a force measuring device. Preferably, a difference between the first angle position and the second angle position is used as an indication for the force exerted by the user.

According to a further preferred refinement the first and second rotational axes coincide, and in particular the actuator is fixedly coupled with the positioning element on a common axis.

This refinement may be provided for in a particularly simple manner.

According to a further preferred refinement the handle and the positioning element are arranged on a common axis which is different from the rotational axis of the actuator.

This refinement allows in a simple manner to provide for a reduction between the rotational movement of the actuator and der rotational movement of the positioning element.

According to a further preferred refinement the force which is transmitted by the actuator onto the positioning element depends on the angular position of the positioning element relative to a rest position or null position of the positioning element. In particular, the force is larger for a large deviation of the angular position of the positioning element from the rest position or null position than for a small deviation. Preferably, a table ("look-up table") is provided which assigns certain angular positions of the positioning element to certain forces to be transmitted by the actuator onto the positioning element, in particular by defining a driving current for the actuator. Thus, a motor support is preferably implemented for the user depending on the current displacement.

According to a further preferred refinement at least one angle measuring device is configured for a contactless detection, where in particular the angular measuring devices are configured for a contactless detection of the angular positions of the manipulating element and the positioning element.

This preferred refinement is independent of the positioning of the first and second rotational axes and presents an advantage over the prior art even if the first and second rotational axes are arranged perpendicular. All refinements and embodiments described above can be implemented using a contactless detection of the angular positions.

It is appreciated that all features explained above or in the following do not have to be applied in the given combination, but may be used in other combinations or even alone without leaving the spirit and scope of the present invention.

BRIEF DESCRIPTION OF THE DRAWINGS

Preferred embodiments are now described in more detail with reference to the figures.

DESCRIPTION OF PREFERRED EMBODIMENTS

Figure 1:
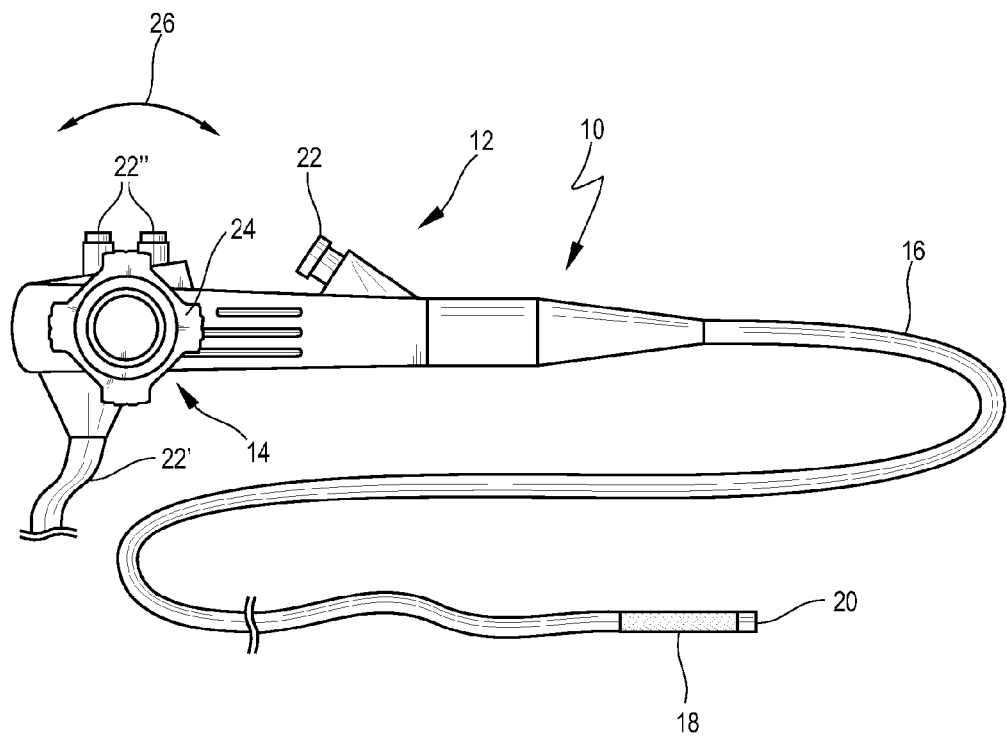
FIG. 1 an embodiment of a flexible endoscope having a deflectable distal section, FIG. 2 the endoscope according to FIG. 1 shown schematically and partially cut open, FIG. 3 a detailed representation of elements of the endoscope of FIG. 1, FIG. 4 a first embodiment of a coupling arrangement of FIG. 3, FIG. 5 a second embodiment of a coupling arrangement of FIG. 3, FIG. 6 the coupling arrangement of FIG. 5 when displacing the first part, FIG. 7 the coupling arrangement according to FIG. 6 after the resulting displacement of the second part, FIG. 8 a further embodiment in a view from the top, FIG. 9 the preferred embodiment of FIG. 8 in a view from the side, FIG. 10 a further embodiment shown in a view from the top, and FIG. 11 an embodiment according to FIG. 10 shown in a view from the side.

FIG. 1 shows an endoscopic instrument 10 having a manipulating piece 12, a manipulating element 14 and a flexible endoscope shaft 16. It is to be appreciated that the explanations in the context of the disclosure apply to a rigid instrument shaft (not shown) as well.

The endoscopic instrument 10 is used for examination and/or surgery purposes in medical procedures. The instrument shaft 16 has, not shown, an endoscope optic embodied as optical fibers, image-conducting cables, different channels, e.g. a suction and a cleaning channel, and an instrument channel. The instrument shaft 16 is proximally connected to the manipulating piece 12 and extends distally to a deflectable section 18 which is in particular an end section.

It comprises an end piece 20 embodied as a terminating socket. The end piece 20 is the portion of the endoscope shaft 16 where the optical fibers, the image-conducting cables and the channels end. The endoscope shaft 16 is only partially shown in the figures. The manipulating piece 12 comprises a connection 22, a supply cable 22' and buttons 22". The connection 22 leads to an instrument channel. Through this channel instruments can be inserted into the endoscope shaft 16 all the way to the end piece 20. This allows to perform surgeries in the area ahead of the end piece 20.

The supply cable 22' contains different kinds of supplies, for example an electric supply, optical fibers, suction and cleaning lines and/or data lines. The image-generating process in the endoscopic instrument 10 is achieved via an imaging sensor, not shown, inside the manipulating piece 12 or in the end piece 20, wherein the image data is routed externally via the supply cable 22', in particular to a camera control unit (CCU), not shown.

The manipulating element 14 is provided for controlling and deflecting the section 18, wherein the corresponding handle 24 is shown which can be rotated in the directions of the couple-headed arrow 26. By turning the manipulating element 14 the deflectable section 18 is being deflected up/down or left/right. Each of the deflections correspond to the direction of rotation of the manipulating element 14 either clockwise or counterclockwise.

Figure 2:
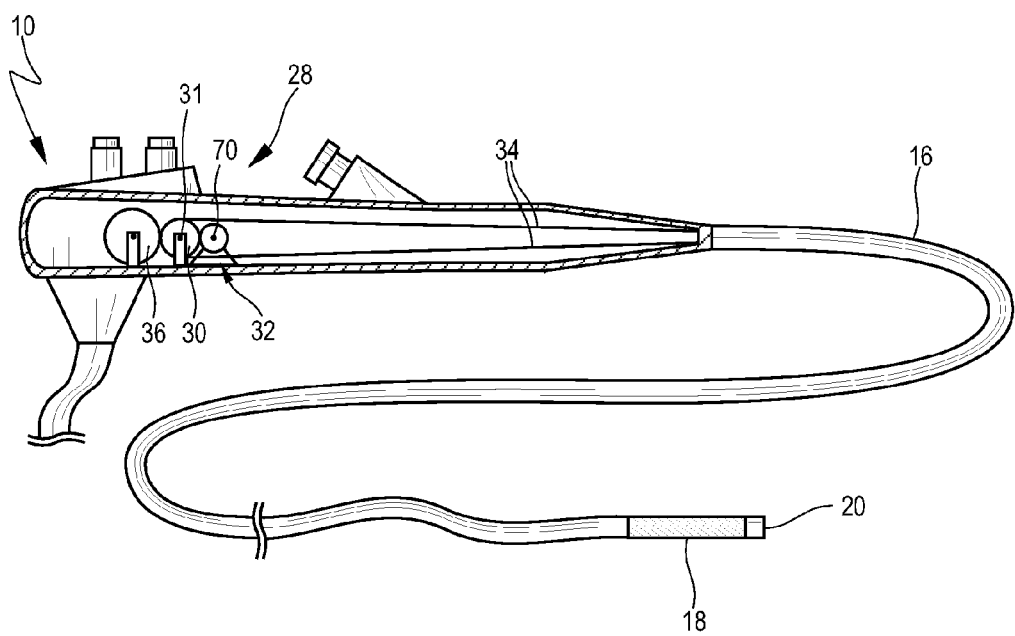

As shown in FIG. 2 a positioning element 30 having a first rotational axis 31 as well as an actuator 32 having a second rotational axis 70 are arranged in a proximal end portion 28 of the manipulating piece 12. The positioning element 30 is connected to a pulling element 34 which extends through the endoscope shaft 16 and reaches into the end section 18. The pulling element 34 is looped around the positioning element 30 and is embodied as one integral piece. Further, an engaging element 36 which is a piece of the manipulating element 14, is shown in the manipulating piece 12.

Figure 3:
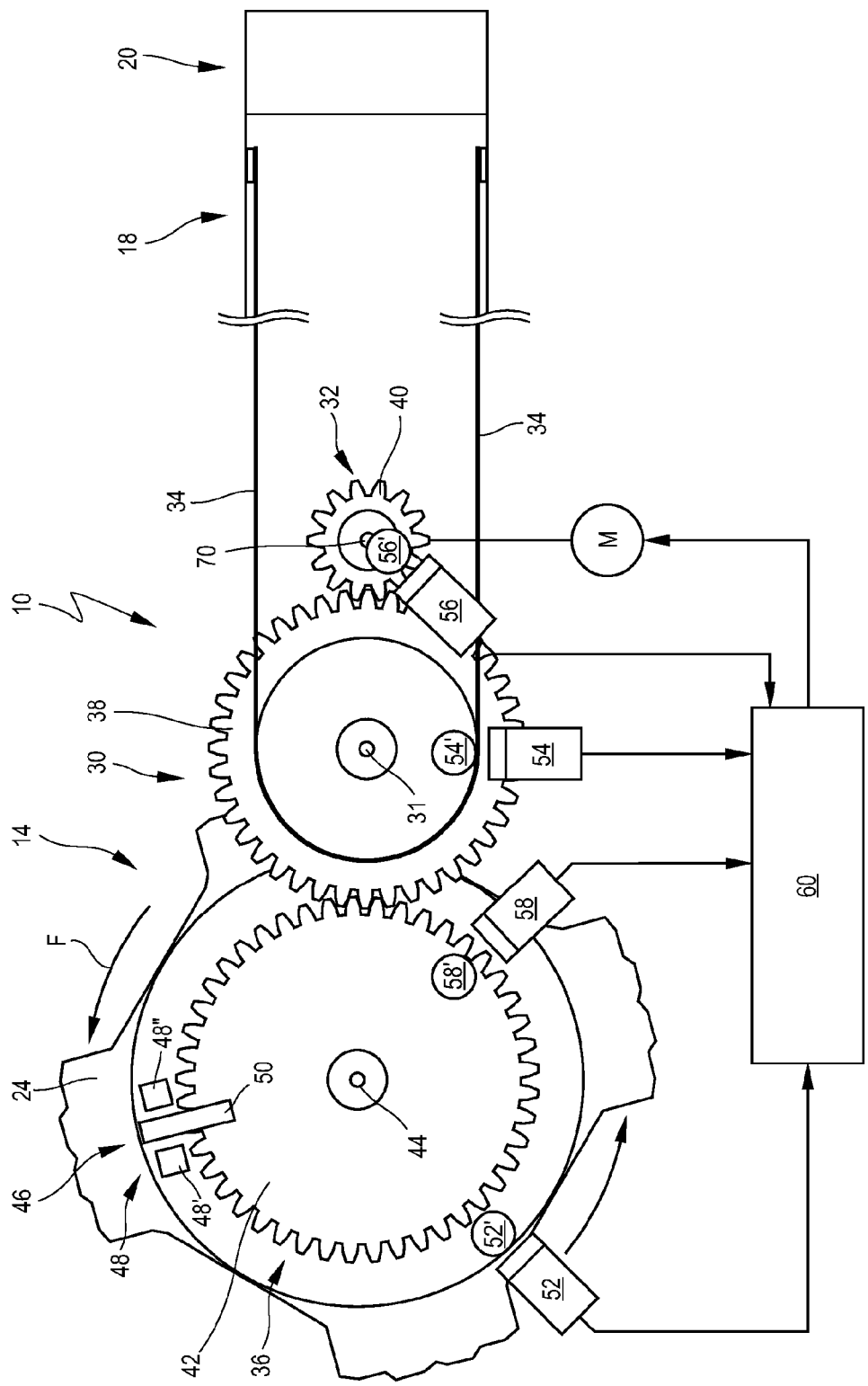

FIG. 3 shows a detailed view of elements comprised in the endoscopic instrument 10 according to FIG. 1. It is shown that the positioning element 30 comprises a first gear ring 38, the actuator 32 comprises a second gear ring 40, and the first and second gear rings 38, 40 are arranged such that their teeth are meshing. The actuator 32 further comprises an electric motor M, and the manipulating element 14 comprises a third gear ring 42 wherein the first and the third gear rings 38, 42 are arranged such that their teeth are meshing. The result is that the manipulating element 14 and the actuator 32 are mechanically operationally connected with one another such that a force F exerted by the user onto the manipulating element 14 may at least partially be transmitted onto the actuator 32.

The handle 24 and the engaging element 36 of the manipulating element 14 are arranged such that they may be relatively displaced to one another. The handle 24 and the engaging element 36 are coupled to one another such that a displacement of the handle 24 may result in a displacement of the engaging element 36. For the shown embodiment the displacements are rotational displacements.

In order to achieve this the handle 24 and the engaging element 36 are arranged along a drive shaft 44 wherein the handle 24 may be rotatorily displaced relative to the engaging element 36 and the drive shaft 44. In order to couple the displacement of the handle 24 and the displacement of the engaging element 36 the manipulating element 14 comprises a coupling arrangement 46 having a first part 48 and a second part 50.

For the embodiment shown the first part 48 is fixedly connected to the handle 24 and the second part 50 is fixedly connected to the engaging element 36. The parts 48, 50 are arranged and embodied such that a transmission of a force between the handle 24 and the engaging element 36 may be effected. The first part 48 comprises two elements 48', 48", and the second part 50 is embodied as a projection which is arranged between the two elements 48', 48". The first and second parts 48, 50 are arranged relative to one another such that a displacement of the first part 48 may result in a displacement of the second part 50.

A first angle measuring device 52 is configured to provide an indication related to a first angle position of the manipulating element 14 or the handle 24. A second angle measuring device 54 is embodied to provide an indication related to a second angle position of the positioning element 30. A third angle measuring device 56 is configured to provide an indication related to a third angle position of the actuator 32. A fourth angle measuring device 58 is configured to provide an indication related to a fourth angle position of the engaging element 36.

For the shown embodiment the angle measuring devices 52, 54, 56, 58 are embodied as Hall-sensors wherein only symbolically a corresponding magnet 52', 54', 56', 58' is shown. The Hall-sensors are an example for a contactless angle measurement which is on its own an improvement over the prior art. The angle measurement may be performed in a contactless manner also via other means, in particularly capacitively or inductively.

The endoscopic instrument 10 further comprises a control device 60 which is embodied to perform one, a plurality of or all of the following functions:

The actuator 32 is driven by taking the first angle position and the second angle position into account.

The actuator 32 is driven by taking the third angle position and the fourth angle position into account.

The actuator 32 is driven by taking the first angle position and the fourth angle position into account.

The actuator 32 is driven such that the positioning element 30 is maintained in a set position when the user does not exert a force F onto the manipulating element 14.

The actuator 32 is driven such that the actuator exerts a force onto the positioning element 30 which is at least in certain ranges at least approximately proportional to the force F which the user exerts onto the manipulating element 14.

The underlying functionality is as follows. It is assumed that the user exerts a force F onto the handle 24 into a counterclockwise direction (when seen from the viewing perspective). The control device 60 detects a change in the first angle positions and/or a difference between the first and the second angle positions. Therefore it is detected that the user exerts a force F onto the handle 24. At least a portion of the force F is transmitted onto the positioning element 30.

The control device 60 detects in which direction the user intends to displace the positioning element 30, here in a clockwise direction, and drives the actuator 32 via the motor M correspondingly. In this particular case, this means that the third gear ring 42 is driven into a counterclockwise direction.

In case of a fault of the actuator 32, the first part 48 continues to transmit at least a portion of the force F onto the second part 50, so that the portion of the force F is transmitted onto the positioning element 30.

At this point it is recalled that according to preferred embodiments the manipulating element comprises a first handle which displaces a first positioning element and a second handle which displaces a second positioning element. An actuation of the first handle results in a first movement of the section, in particular a movement left/right, and an actuation of the second handle results in a second movement of the section, in particular a movement up/down. Preferably one of the handles is arranged on a hollow drive shaft in which a drive shaft of the other handle is arranged. Therefore, certain embodiments may comprise two or more handles, positioning elements and actuators.

Figure 4:
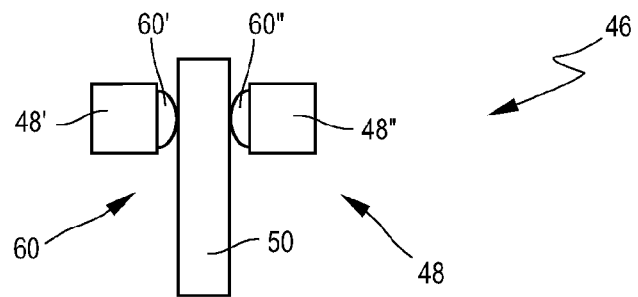

FIG. 4 shows a second embodiment of a coupling arrangement 46 having a force measuring device 60', 60". In a preferred embodiment the force measuring device 60', 60" indicates whether a force is exerted between the first part 48 and the second part 50. In a further preferred embodiment the force measuring device 60', 60" provides for an indication related to the magnitude of a force exerted between the first part 48 and the second part 50. Preferably the first part 48 and the second part 50 are in direct contact via the force measuring device 60', 60", so that the user receives a feedback when actuating the manipulating element 14.

Figure 5:
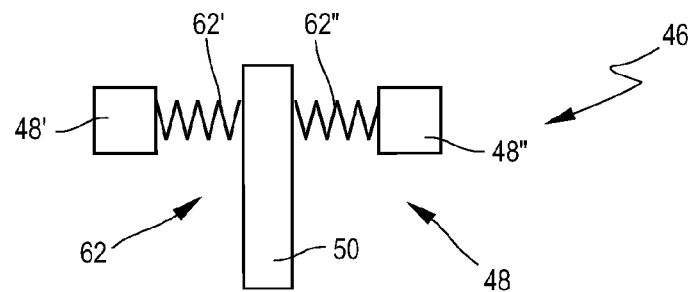

FIG. 5 shows a third embodiment of a coupling arrangement 46. In this embodiment a spring device 62 with spring elements 62', 62" is arranged at the first part so that a force between the first part 48 and the second part 50 is transmitted via the spring device 62.

Figure 6:
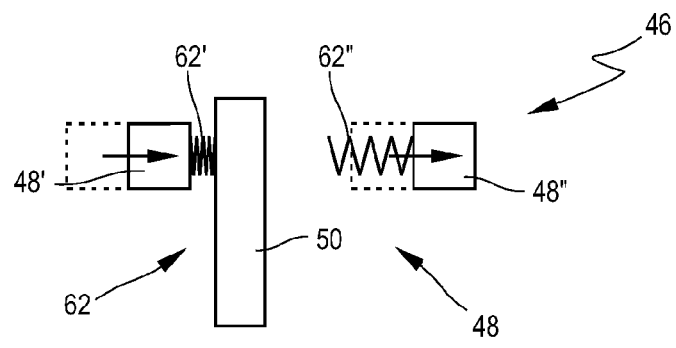

FIG. 6 shows the situation when the first part 48 has been displaced relative to the second part 50. The second spring element 62" is tensioned so that the user obtains a feedback. Again, the actuator 32 is driven based on the angle information as previously explained.

Figure 7:
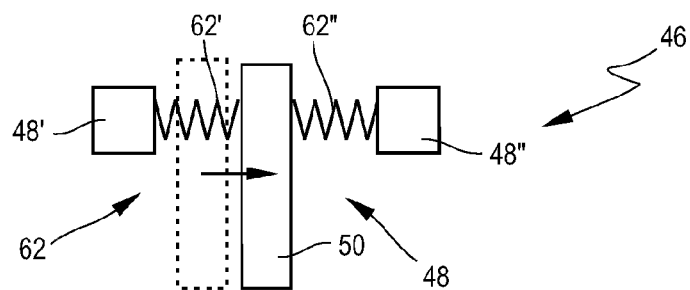

FIG. 7 shows the rest position after the engaging element 36 has reached the position which the user has determined via the handle 24.

Figure 8:
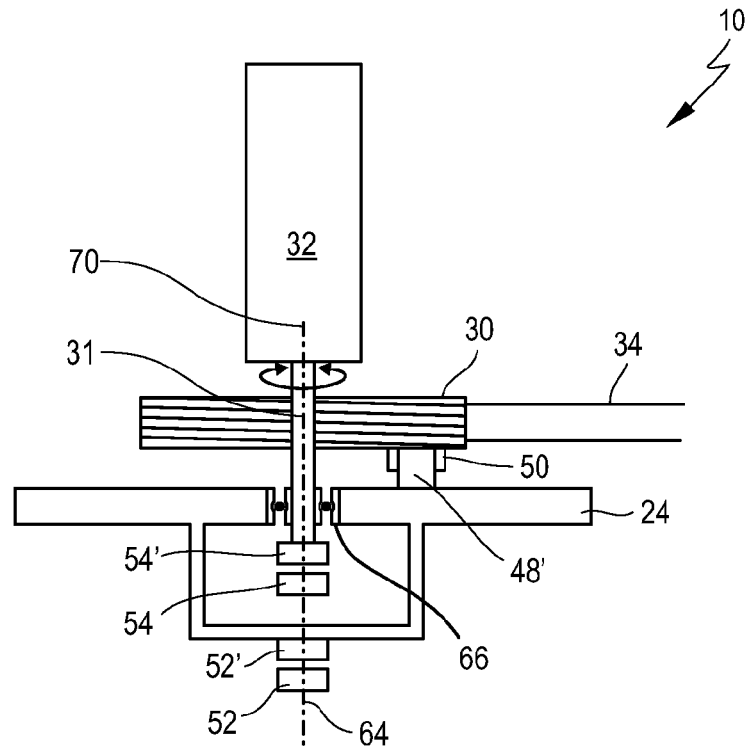

FIG. 8 shows a further embodiment where the first and second rotational axes coincide by the actuator 32 being fixedly coupled on a common axis 64 with the positioning element 30. The previously presented reference numerals and the corresponding explanations to the individual elements apply correspondingly. In contrast to the embodiment according to FIG. 3, no gear rings are required. Further, the handle 24 is also arranged on the axis 64 via a bearing 66.

Figure 9:
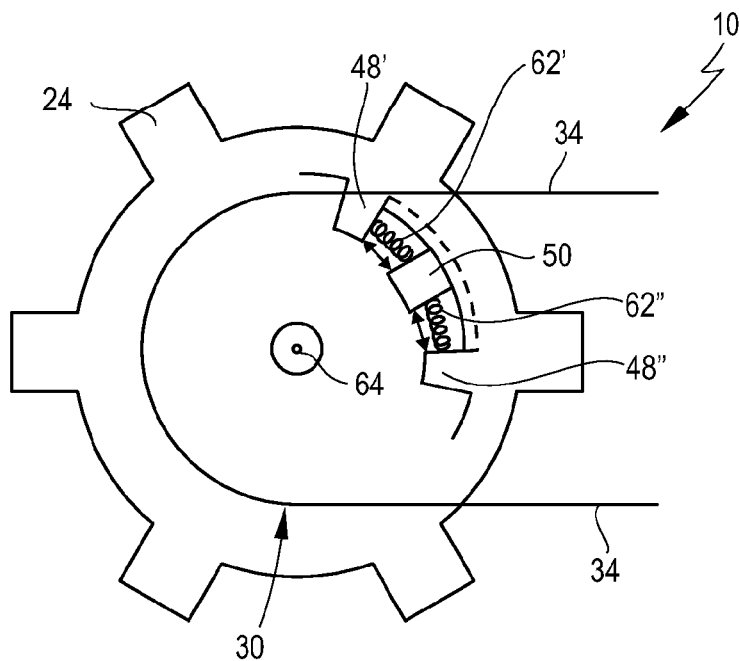

FIG. 9 shows the embodiment according to FIG. 8 in a view from the side.

Figure 10:
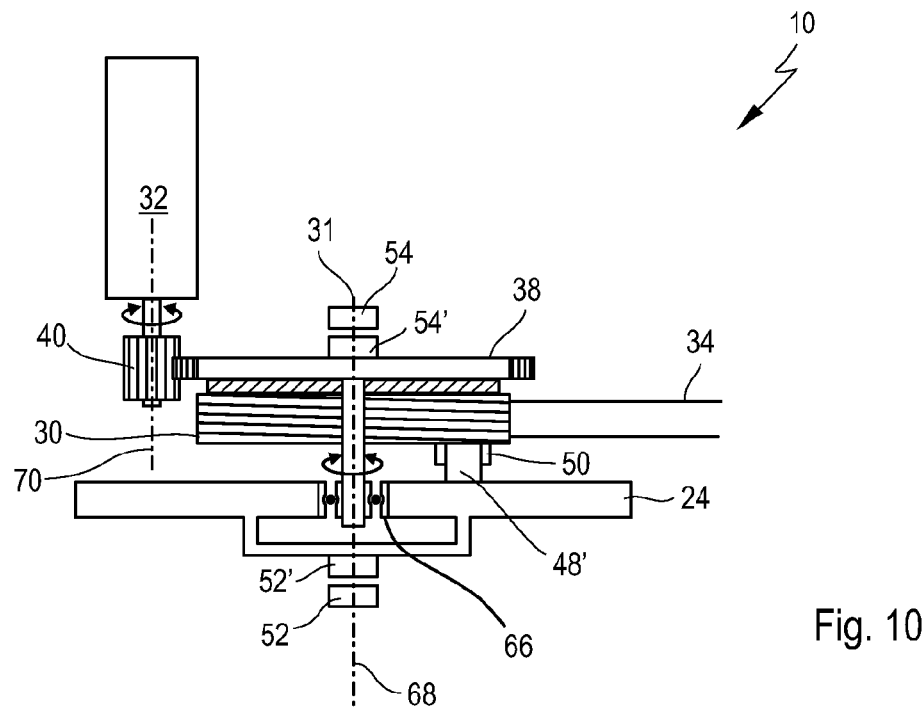

FIG. 10 shows yet a further embodiment where the handle 24 and the positioning element 30 are arranged on a common axis 68 which is different from a rotational axis 70 of the actuator 32. This embodiment may be easily implemented, however still provides the opportunity of arranging a reduction between the actuator 32 and the positioning element 30, here, between the first gear ring 38 and the second gear ring 40. The first and second rotational axes 31, 70 are substantially parallel.

Figure 11:
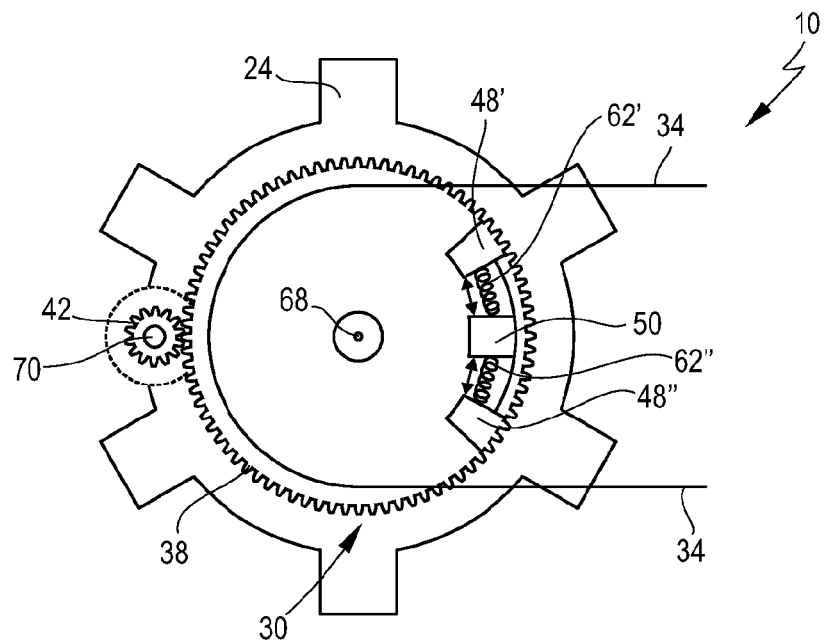

FIG. 11 shows the embodiment according to FIG. 10 in a view from the side.

What is claimed is:

1. An endoscopic instrument comprising:
   a manipulating piece having a manipulating element comprising a coupling arrangement having a first part and a second part, the first part and the second part having a variable distance between each other during operation of the endoscopic instrument;
   an instrument shaft having a section to be manipulated by a user, wherein the instrument shaft is coupled to the manipulating piece;
   a positioning element having a first rotational axis;
   a handle;
   a pulling element mechanically coupled to the positioning element and the section of the instrument shaft, such that a displacement of the positioning element may achieve an actuation of the section of the shaft by transmitting a force via the pulling element; and
   an actuator coupled to the positioning element, such that an actuation of the actuator may provide for a displacement of the positioning element by transmitting a force from the actuator to the positioning element, wherein the actuator comprises a second rotational axis,
   wherein the manipulating element is configured such that a user may displace the positioning element by actuating the manipulating element,
   wherein the manipulating element is mechanically coupled to the positioning element such that a force exerted by the user onto the manipulating element may at least be partially transferred onto the positioning element and may provide for a displacement of the positioning element,
   wherein the first rotational axis and the second rotational axis are arranged at an angle of less than 90° relative to one another,
   wherein one of the first and second parts of the coupling arrangement is connected to the handle and the other one of the first and second parts is connected to the positioning element, wherein the parts are configured and arranged such that a transmission of a force between the handle and the positioning element may be effected.

2. The endoscopic instrument of claim 1, wherein the positioning element comprises a first gear ring, the actuator comprises a second gear ring, and the first and second gear rings are coupled by force-fit.

3. The endoscopic instrument of claim 1, wherein the positioning element comprises a first gear ring, the manipulating element comprises an additional gear ring, and the first gear ring and the additional gear rings are coupled by force-fit.

4. The endoscopic instrument of claim 1, wherein the manipulating element and the actuator are mechanically operationally coupled to one another such the force exerted by the user onto the actuating element may at least be partially transmitted onto the actuator.

5. The endoscopic instrument of claim 1, wherein the manipulating element comprises a handle and an engaging element, the handle and the engaging element being arranged such that they can be displaced relatively to one another, and the handle and the engaging element are coupled with one another such that a displacement of the handle may result in a displacement of the engaging element.

6. The endoscopic instrument of claim 1, wherein the coupling arrangement comprises a force measuring device configured to indicate whether a force is being exerted between the first part and the second part or to provide an indication related to the magnitude of a force exerted between the first part and the second part.

7. The endoscopic instrument of claim 1, wherein the first part comprises two elements and the second part is embodied as a projection being arranged between the two elements, and the first and the second parts are arranged relative to one another such that a displacement of the first part may result in a displacement of the second part.

8. The endoscopic instrument of claim 1, further comprising a first angle measuring device embodied to provide an indication of a first angle position of a handle of the manipulating element and/or a second angle measuring device embodied to provide an indication of a second angle position of a positioning element.

9. The endoscopic instrument of claim 8, further comprising at least one angle measuring device configured for a contactless detection.

10. The endoscopic instrument of claim 8, further comprising at least one angle measuring device configured for a contactless detection of the angle position of the manipulating element and the positioning element.

11. The endoscopic instrument of claim 1, further comprising a control device configured to drive the actuator taking into account a first angle position of a handle of the manipulating element and a second angle position of a positioning element.

12. The endoscopic instrument of claim 1, further comprising a control device configured to drive the actuator such that the positioning element is maintained at a given position if the user does not exert a force on the manipulating element.

13. The endoscopic instrument of claim 1, further comprising a control device configured to drive the actuator such that it exerts a force onto the positioning element which is at least in certain ranges at least approximately proportional to the force which the user exerts onto the manipulating element.

14. The endoscopic instrument of claim 1, wherein the first and second rotational axes coincide.

15. The endoscopic instrument of claim 1, wherein the handle and the positioning element are arranged on a common axis which is different from the rotational axis of the actuator.

16. The endoscopic instrument of claim 1, wherein the first rotational axis and the second rotational axis are at least approximately parallel to one another.

17. An endoscopic instrument comprising:
a manipulating piece having a manipulating element comprising a coupling arrangement having a first part and a second part, the first part and the second part having a variable distance between each other during operation of the endoscopic instrument;
an instrument shaft having a section to be manipulated by a user, wherein the instrument shaft is coupled to the manipulating piece;
a positioning element having a first rotational axis;
a pulling element coupled to the section;
a handle; and
an actuator coupled to the positioning element, the actuator comprising a second rotational axis,
wherein the manipulating element is configured for displacing the positioning element by actuating the manipulating element,
wherein the manipulating element is mechanically coupled to the positioning element,
wherein the first rotational axis and the second rotational axis are arranged at an angle of less than 90° relative to one another,
wherein one of the first and second parts of the coupling arrangement is connected to the handle and the other one of the first and second parts is connected to the positioning element, wherein the parts are configured and arranged such that a transmission of a force between the handle and the positioning element may be effected.

18. An endoscopic instrument comprising:
a manipulating piece having a manipulating element comprising a coupling arrangement having a first part and a second part, the first part and the second part having a variable distance between each other during operation of the endoscopic instrument;
an instrument shaft having a section to be manipulated by a user, wherein the instrument shaft is coupled to the manipulating piece,
a positioning element having a first rotational axis,
a pulling element coupled to the section,
a handle;
an engaging element coupled to the positioning element; and
an actuator coupled to the positioning element, the actuator comprising a second rotational axis,
wherein the manipulating element is configured for displacing the positioning element by actuating the manipulating element,
wherein the manipulating element is mechanically coupled to the positioning element,
wherein the first rotational axis and the second rotational axis are arranged at an angle of less than 90° relative to one another,
wherein one of the first and second parts of the coupling arrangement is connected to the handle and the other one of the first and second parts is connected to the engaging element, wherein the parts are configured and arranged such that a transmission of a force between the handle and the engaging element may be effected.

\* \* \* \* \*